United States Patent [19]
Uddén et al.

[11] Patent Number: 5,180,907
[45] Date of Patent: Jan. 19, 1993

[54] METHOD AND APPARATUS FOR THE MEASUREMENT OF RAPID LIGHT VARIATION SUPERIMPOSED ON A SLOWLY CHANGING BACKGROUND LIGHT INTENSITY

[76] Inventors: Per Uddén, Hofstrasse 1, CH-6064 Kerns, Sweden; Jan K. Ober, ul Brzechwy 6, PL-60-195 Poznan, Poland

[21] Appl. No.: 469,540
[22] PCT Filed: Sep. 21, 1988
[86] PCT No.: PCT/SE88/00486
§ 371 Date: Apr. 9, 1990
§ 102(e) Date: Apr. 9, 1990
[87] PCT Pub. No.: WO89/02585
PCT Pub. Date: Mar. 23, 1989

[30] Foreign Application Priority Data
Sep. 21, 1987 [SE] Sweden ............... 8703637
Sep. 21, 1987 [SE] Sweden ............... 8703638

[51] Int. Cl.⁵ ............................................. G01J 1/32
[52] U.S. Cl. ................................. 250/205; 250/221; 250/214 B; 351/210
[58] Field of Search ............... 250/205, 221, 214 B, 250/214 C; 351/210, 209

[56] References Cited
U.S. PATENT DOCUMENTS

| | | | |
|---|---|---|---|
| 4,260,882 | 4/1981 | Barnes | 250/205 |
| 4,273,999 | 6/1981 | Pierpoint | 250/205 |
| 4,720,189 | 1/1988 | Heynen et al. | 351/210 |
| 4,812,642 | 3/1989 | Hasegawa et al. | 250/205 |

FOREIGN PATENT DOCUMENTS

| | | |
|---|---|---|
| 0115122 | 8/1984 | European Pat. Off. . |
| 2111197 | 6/1983 | United Kingdom . |
| 86/03113 | 6/1986 | World Int. Prop. O. . |

*Primary Examiner*—David C. Nelms
*Assistant Examiner*—K. Shami
*Attorney, Agent, or Firm*—Oblon, Spivak, McClelland, Maier & Neustadt

[57] ABSTRACT

The invention relates to measurements of light, where light variations superimposed on a background amount of light, which is changing relatively slowly, are measured. To give the light sensitive element (3,3') used a stable operational point a light emitting element (5,5') is used for injecting extra light into the light sensitive element (3,3'). Thus, the amount of light injected by this light emitting element (5,5') is chosen in such a way that the sum of the ambient light and the injected light is substantially constant. To this amount of light are added the light variations, e.g. caused by a second light emitting element (9,9'). This process and device can be used in a device for measuring the eye movements of a person.

21 Claims, 5 Drawing Sheets

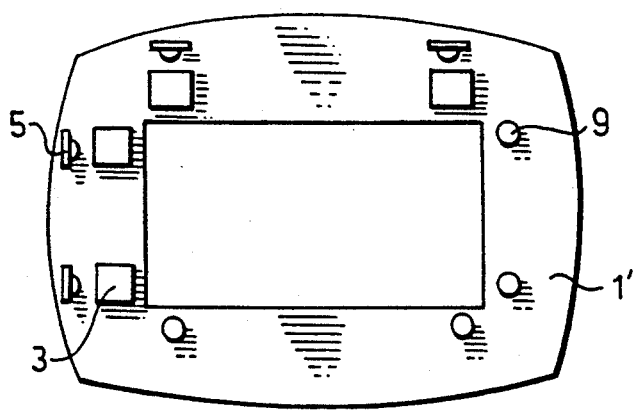
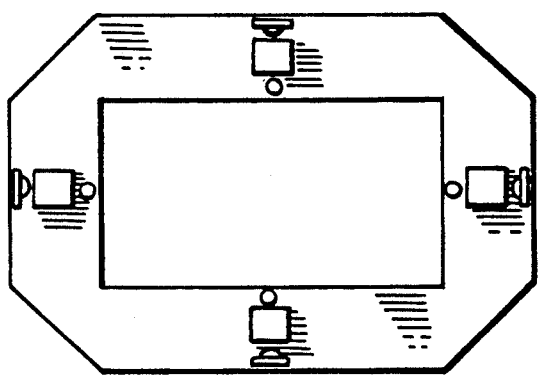
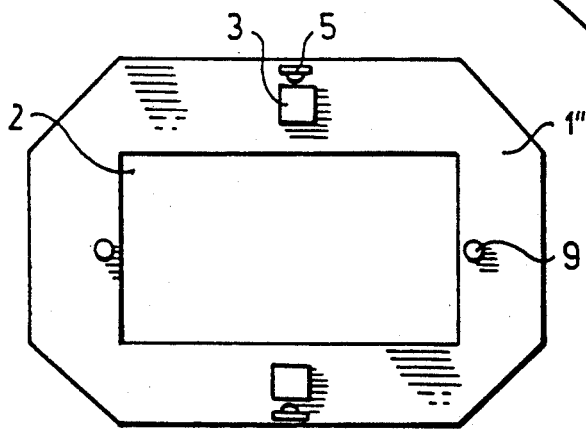
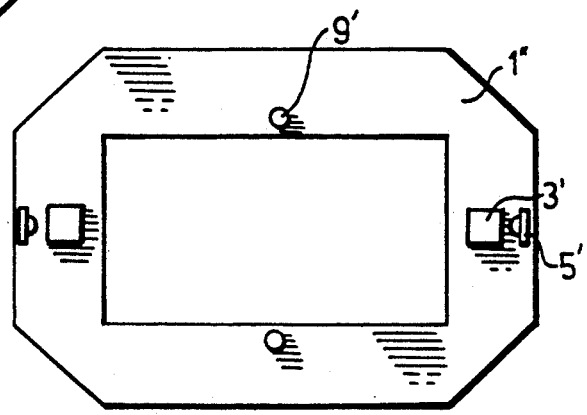

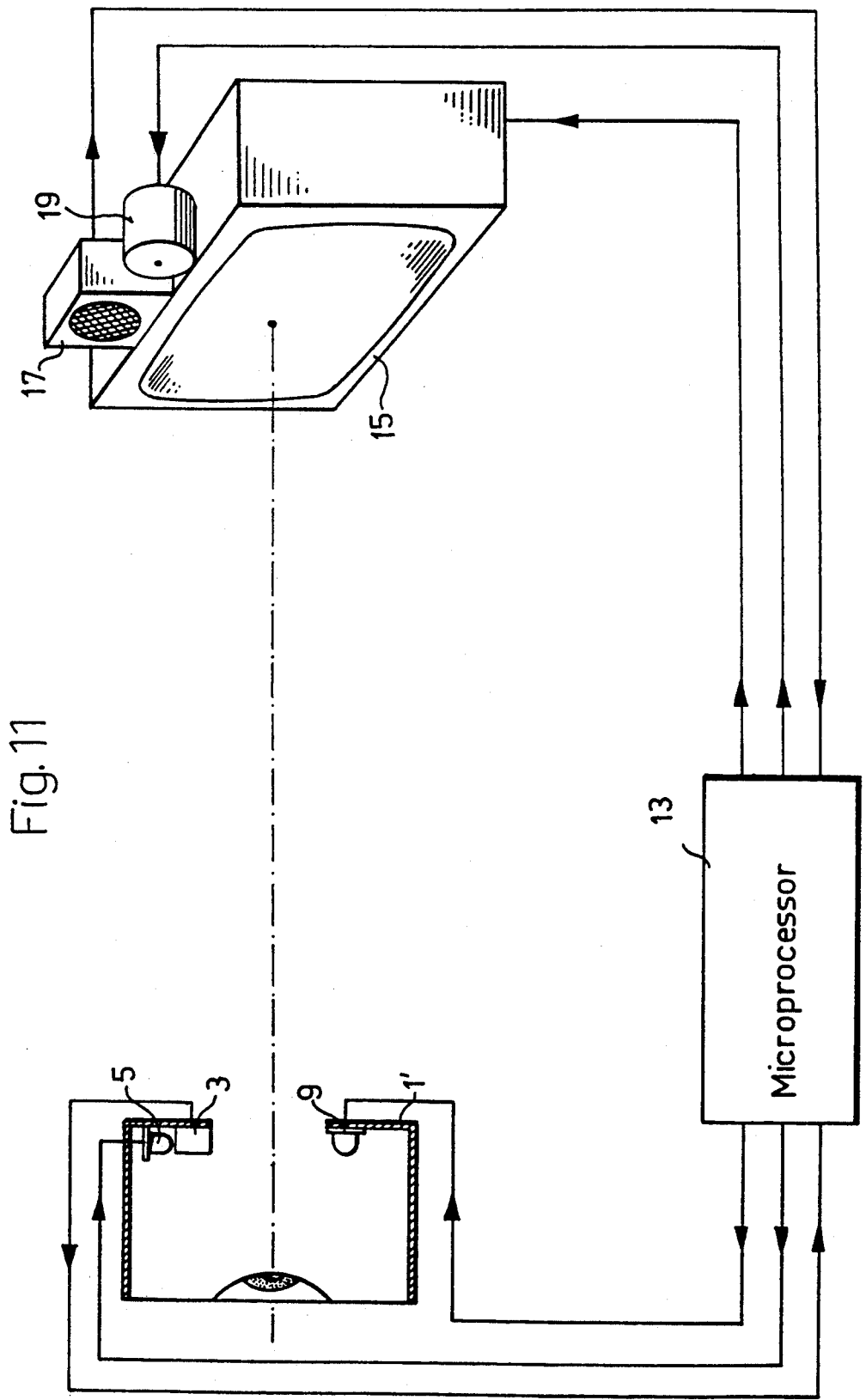

METHOD AND APPARATUS FOR THE MEASUREMENT OF RAPID LIGHT VARIATION SUPERIMPOSED ON A SLOWLY CHANGING BACKGROUND LIGHT INTENSITY

The present invention relates to measuring intensity variations of light, visible and/or not visible to the human eye, preferably not visible, such as IR-light. The invention is particularly intended for use in a system for measuring eye movements but is not limited to this field of application.

In measuring the amount of light or other similar radation, light sensitive detectors as photo diodes or photo transistors can be used. These elements are usually not linear, i.e. the delivered electric signal is not directly proportional to the amount of incident light upon the detector surface. This means that the curve of the corresponding electric signals, e.g. a voltage E, has to be determined as a function of the amount of incident light O. In this way a precise measurement of the amount of light could be obtained. However, this procedure is complicated, and in automatic use the detector has to be supplemented with an electronic calculating device, e.g. a microprocessor, to deliver the desired proportional electric signal.

These measurements are normally performed when recording the eye movements of a person. In this procedure, generally, infrared light is emitted from a light emitting element placed in front of the eye and the reflected light is detected by an infrared sensitive light detecting element. The total amount of light incident upon the person's eye is composed of the ambient light and the light reflected by the eye. This reflected light is caused essentially by the light emitted by the light emitting element. When the intensity of the ambient light changes, however, the light detecting element has to be recalibrated to compensate it. The above mentioned lack of linearity in most commercially available photo sensitive elements makes this recalibration complex.

To overcome the above mentioned difficulties, the invention purposes a process and a device for measuring variations in light intensity, the characteristics of which are set out in the appended claims.

Thus, it is suggested that an extra light emitting element is arranged to emit some extra light directly into said light sensitive element. This extra light is controlled to give the light sensitive element a predetermined, stable operational point. In this way the variations of light intensity are always taken from a fixed point on the characteristic curve of said light sensitive element.

In practical use it is supposed that the incident light is composed of background light, which is almost constant or changing relatively slowly, and rapidly changing light variations. By suitable means, e.g. electronic circuitry, some of the background light and the injected extra light is controlled to be constant. This can most easily be done when said light variations are known to be equal to zero in predetermined time intervals. If the light detector output is changed from one interval to another, the injected light is changed to keep this output signal constant.

Instead of maintaining a stable operational point for the light detector it can, by means of the extra light injected by the extra light emitting element, be arranged in such a way that the measuring process always is performed for light values on a linear portion of the characteristic curve of the light sensitive element. In periods where the rapidly changing light variations are known to be equal to zero, the injected extra light is changed stepwise with steps of known sizes. By comparing the output signals delivered by the light sensor, to the value obtained without the injected light it can easily be seen if the output values either are proportional to the total amount of light incident upon the light sensitive element or if they at least are located on a linear portion of the characteristic.

In an embodiment of the invention the light sensitve element is substantially planar, e.g. rectangular, and the first light emitting element is then placed adjacent to and facing one edge or side, preferably the long side, of the light sensitive element.

When using the invention for measuring eye movements, a supporting frame with for instance a rectangular opening therein, is used. On the side of the support facing the person's eye said first light emitting element and said light sensitive element are placed. Then it is preferred that the measurement of the eye movements are made by means of a second light emitting element, which could be placed on the opposite side of the rectangular opening in the support. In the latter case at least two similar measuring sets arranged at a distance from each other could be used to give a more correct measurement of the eye movements.

This is the kind of device which is described in the published International Application WO 86/03113, and in this generally, the eye movements in a special direction are measured, but obviously more light detecting and emitting elements could be arranged on the frame to permit measurement of the eye movements in more directions. However, when the eye moves in a direction, which is appropriate for measuring by means of a special set of light emitting elements and detecting elements, also, the other light emitting and detecting elements are influenced. It will require a complex calibration to separate these influences from each other.

To minimize this interference or "cross-talk" between different sets of light detecting elements and emitting elements, it is also proposed another way of arranging and connecting these light emitting elements and detecting elements.

Thus, to measure the movements of the eye in a special direction a set of cooperating light emitting and detecting elements is provided where the detecting elements could be provided with cooperating light injecting elements but this proposed arrangement may also be used without light injection. This set generally has its light detecting elements located in parallel to said direction and its light emitting elements, which provide light pulses to be detected by these associated detecting elements, are arranged in a direction substantially or approximately perpendicular to the direction of the light detecting elements. One or preferably two or more such sets are provided according to the invention.

In a suitable embodiment for measuring the eye movement in one direction, every set of associated light emitting elements and light detecting elements comprises two light emitting elements and two light detecting elements, arranged symmetrically in respect of the eye. This means that this set has a mirrorlike symmetry with respect both to the planes passing through the light emitting elements and the light detecting elements.

When two sets of operating light emitting and detecting elements are provided, these are preferably arranged orthogonally to each other or near this position.

In this way the different eye movements can easily be separated from each other.

For this it is more precisely suggested a device for measuring the movements of an eye comprising light emitting and detecting elements located at a distance from said eye and characterized in that it comprises for measuring the eye movements in a first direction first light detecting elements, located in a first symmetry plane of the eye and containing said first direction, and first light emitting elements, arranged to cooperate, in the detection of the movements of the eye, with said first detecting elements and located in a symmetry plane of the eye, being essentially orthogonal to said first symmetry plane.

Also, in this device said first light detecting elements may be two and may be located symmetrically with respect to the eye and also said first light emitting elements may also be two and may be located symmetrically with respect to the eye.

This device may also comprise for measuring the eye movements in a second direction, not coincident with the first direction, second light detecting elements, located in a second symmetry plane of the eye and containing said first direction, and second light emitting elements, arranged to cooperate, in the detection of the movements of the eye, with said second light detecting elements and located in a symmetry plane of the eye, being essentially orthogonal to said second symmetry plane.

Also, in this device said second light detecting elements may be two and may be located symmetrically with respect to the eye and said second light emitting elements may also be two and may be located symmetrically with respect to the eye.

In this case said second direction may be essentially perpendicular to the first direction.

More generally this device for measuring the movements of an eye comprising light emitting and detecting elements located at a distance from said eye may comprise for measuring the eye movements in several different directions, for each chosen one of said directions, light emitting elements, located in a symmetry plane of the eye and containing the chosen direction, and light emitting elements, arranged to cooperate, in the detection of the movements of the eye, with said light detecting elements, associated with the chosen direction, and located in a symmetry plane of the eye, being essentially or at least approximately orthogonal to said symmetry plane, associated with the direction chosen.

In this device further said light detecting elements, associated with the direction chosen, may be two and may be located symmetrically with respect to the eye and said light emitting element, associated with the direction chosen, may also be two and may be located symmetrically with respect to the eye.

The invention also contemplates a process for measuring the movements of a person's eye comprising illuminating the eye with light pulses, measuring the light reflected by the eye during a part time period of said pulses, measuring the light reflected during the time between said pulses when the eye is not illuminated by said pulses and is only illuminated by the ambient light, evaluating the measured values obtained to provide first rough values of the eye movement and values indicating the movement of the person's head, correcting, by means of said values for the head movement, the first rough values of the eye movement to provide second corrected values of the movement of the eye.

The signals obtained in the measurement are easily calibrated by first having the eye look at fixed points the positions of which are known and then looking at one fixed spot while moving the head. During this head movement the eye and the head will move in opposite directions and the angular amount of the movements will be related geometrically.

The invention will now be described with reference to the accompanying drawings in which.

Figure 3:
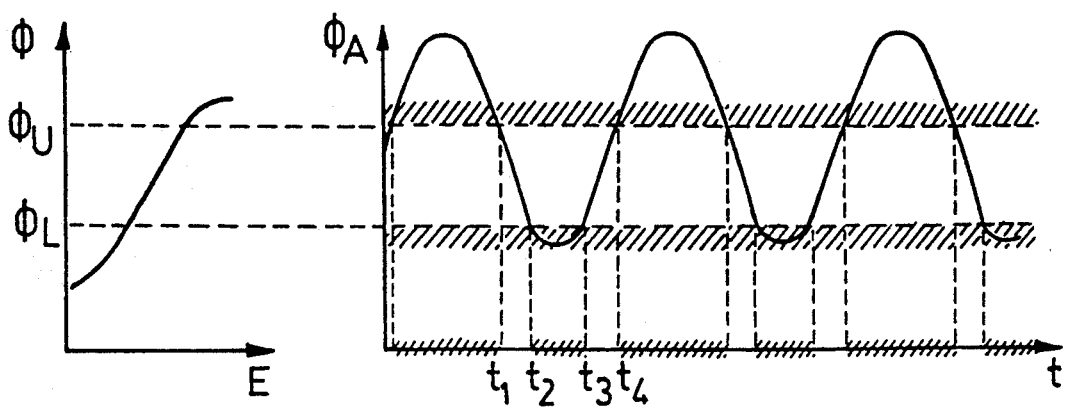
Figure 4:
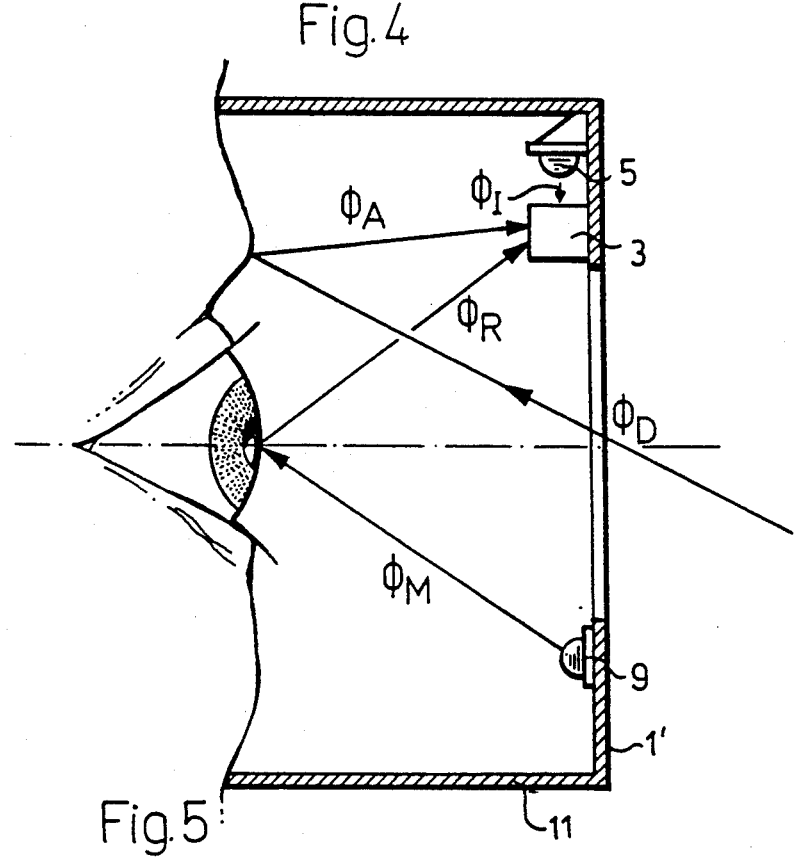
Figure 5:
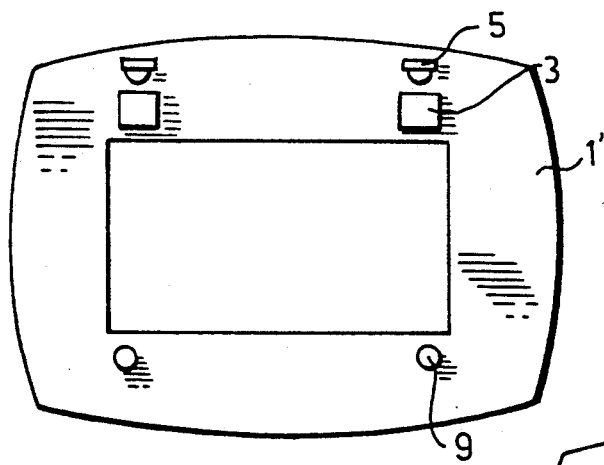
Figure 6:
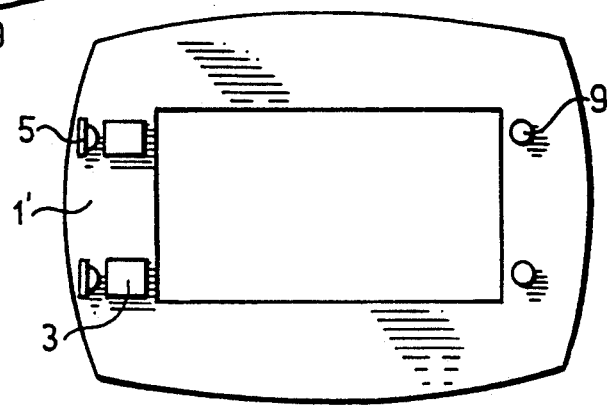
Figure 12:
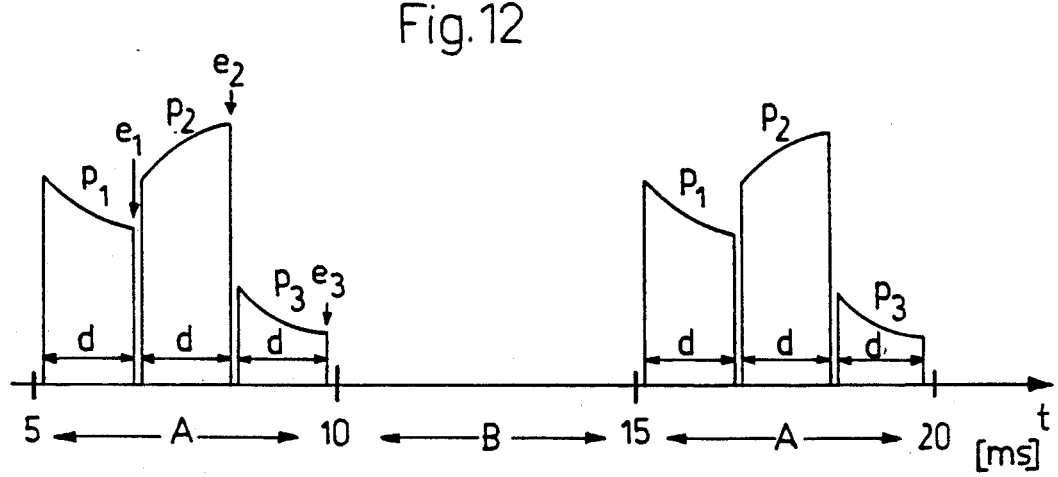
Figure 13:
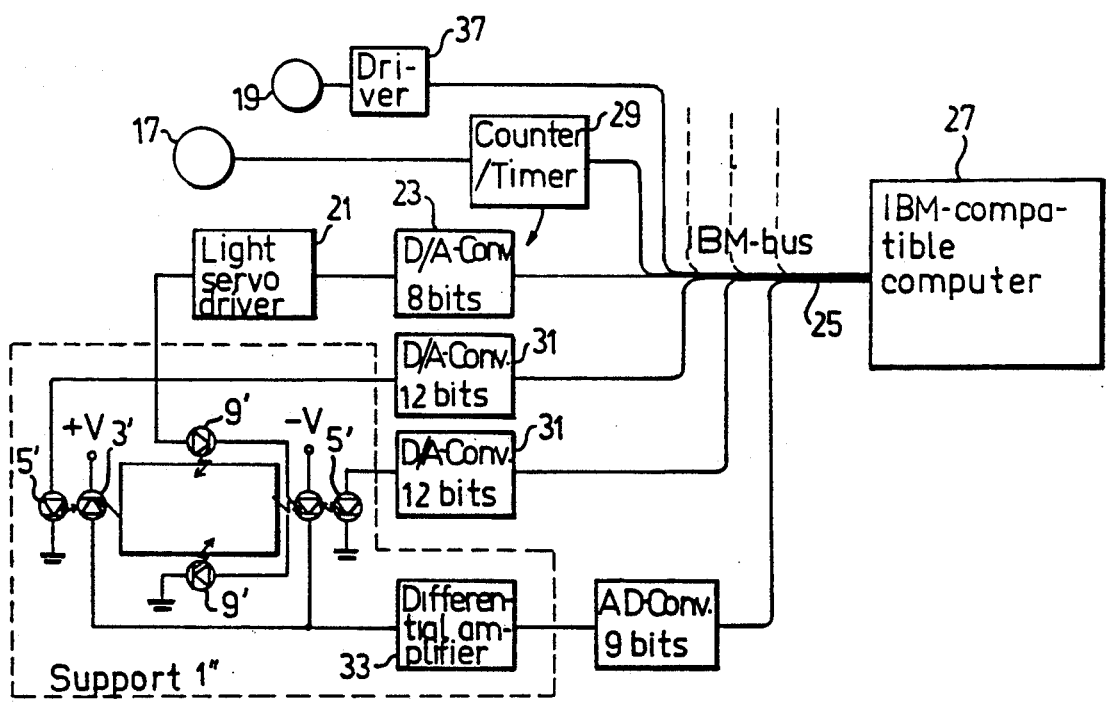

FIG. 3 shows two diagrams, the left diagram illustrating a typical characteristic curve of a light sensitive element and the right diagram illustrating the variations or fluctuations of ambient light caused by the conventional AC mains supply, FIG. 4 is a view from the side schematically illustrating an eye movement measuring device, FIG. 5 is a front view, seen from the eye, of a device for measuring eye movements in a horizontal direction, FIG. 6 is similar to FIG. 5, but showing a device intended for measuring the eye movement or position of the eye in the vertical direction, FIG. 7 is an eye position measuring device adapted to measure the position of an eye both in the horizontal and the vertical direction, and FIG. 8 is a schematical view of a device for measuring the eye movements in two independent directions, FIG. 9 is a view of a device for measuring the eye movements in a vertical direction, FIG. 10 is a view of a device for measuring the eye movements in a horizontal direction, FIG. 11 illustrates schematically the invention used in a combined system for measuring both the movements of an eye and the head movements, FIG. 12 is a schematical diagram illustrating how the measuring pulses are spaced in time, FIG. 13 is a schematical block diagram illustrating the most important electronic components of the system.

Figure 1:
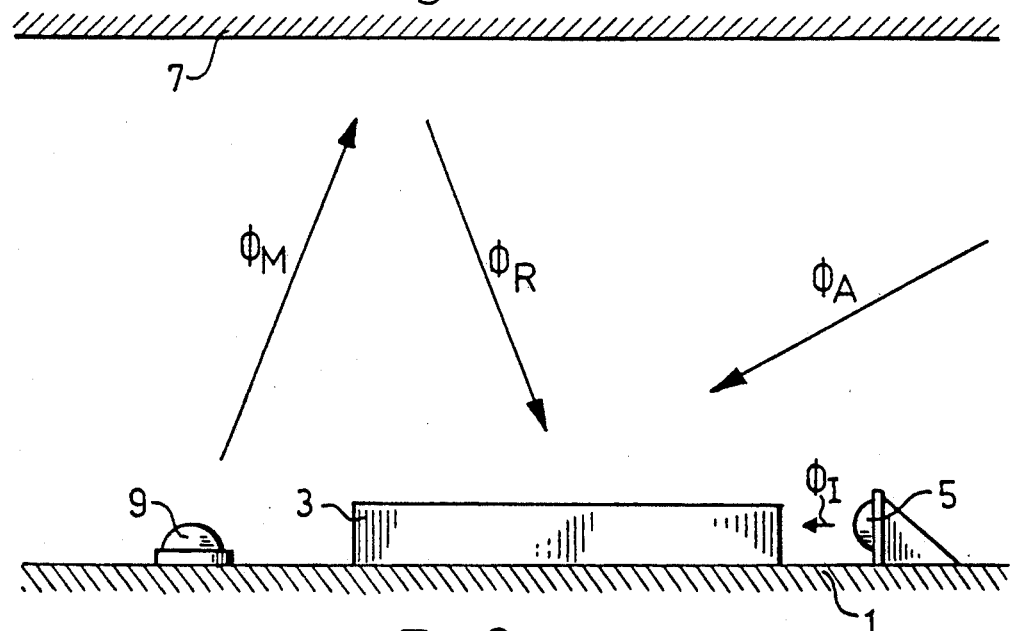
FIG. 1 is a schematical view of the device according to the invention.

In FIG. 1 is illustrated a supporting surface 1, e.g. a supporting frame for an eye movement measurement device. On this support 1 an element 3 is mounted, which is sensitive to the type of variation in question, for instance infrared light used in eye movement measurements. This element 3 is rather thin and can generally have a rectangular shape. It is for instance a photo diode or a photo transistor, which is suitably connected to appropriate electric driving sources. At some distance from or adjacent to this light sensitive element 3 a first light emitting element 5 is located. This can be a light emitting diode and can suitably be directed to illuminate the surface of the light sensitive element 3 from the side. The total light incident on to the surface of the light emitting element 3 is in this case only the ambient light $\phi_A$ and the light $\phi_I$ emitted from or ejected by the first light emitting means 5. The device is intended for measuring variations in the incident light, preferably small variations compared to the background light $\phi_A$. These variations can be the light $\phi_R$ reflected by a surface 7. This surface 7 is, in an eye movement measurement operation, a part of the surface of the eye. The light $\phi_R$ reflected by the surface 7 origins from the second light emitting element 9, which might be placed on the same surface 1 as the light sensitive element 3 and the first light emitting means 5. This light emitting element 9 may also be a LED and it is mounted to output its radiation in a suitable direction, e.g. so that is does not directly illuminate the surface area of the light sensitive element 3. This second light emitting element is also connected to suitable driving circuits, which for instance will cause some periodical light signals to be delivered by the light emitting means 9.

In this case the total amount of light $\phi_T$ received by the light sensitive element 3 is composed, as before, of the ambient light $\phi_A$, the light $\phi_I$ injected from the extra light element 5 as well as the light amount $\phi_R$ reflected from the surface 7. According to the invention the injected amount of light $\phi_I$ is chosen in such a way that the amount $\phi_A + \phi_I$, i.e. the sum of the ambient light and the injected light, is substantially constant.

Figure 2:
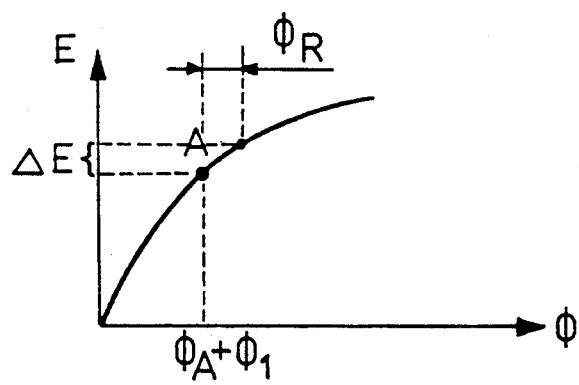
FIG. 2 is a typical characteristic of a photosensitive unit.

This can be further illustrated as in FIG. 2. Here is depicted the characteristic curve of the light detecting element 3 with the delivered voltage E plotted versus the total amount of incident light $\phi_T$. This curve is generally not linear but is curved, e.g. as is shown in FIG. 2. The operational point A of the detecting device is made to remain at the same place on the curve by the process according to the invention. If in contrast the extra light emitting element 5 would not be there, the operational point A would only correspond to the incident ambient light $\phi_A$. Since this amount of ambient light in most cases is submitted to smaller or greater variations which are relatively long in time the operational point A also will be displaced along the characteristic. This means that the output signal E, which corresponds to the reflected light $\phi_R$, will vary even if the amount $\phi_R$ is constant. By the addition of the extra light injecting means 5 this effect is apparently avoided.

The invention will now be described specifically with reference to an eye movement measuring device.

When operating in daylight conditions, the ambient light $\phi_A$ has a constant or slowly varying value. In most cases, however, an eye measurement operation is performed with artificial illumination powered by an electrical AC source of e.g. 50 Hz. This will mean that the ambient light will fluctuate in the way illustrated in the right diagram of FIG. 3. Here a periodically varying light fluctuation of 100 Hz is superposed on a constant or slowly varying light value. As mentioned above the light detector used only has a limited range of operation where its characteristic is linear. This is shown in the left diagram of FIG. 3, where the upper limit $\phi_U$ and the lower limit $\phi_L$ of the linear portion of the characteristic are indicated. As is also indicated in FIG. 3, this linear range of the light detector element will coincide, during only certain time periods, with the ambient illumination of artificial origin. This means that the light detector element only can be used during limited time periods such as between the times $t_1$ and $t_2$ or $t_3$ and $t_4$ respectively in the right diagram of FIG. 3. By providing an additional sensor, which either directly measures the ambient light or senses the light variations by sensing the period of the mains supply, the measurements could always be undertaken during periods, when the ambient light has the desired size, i.e. falls within the linear range of the light detecting elements used. Generally, these measurements are very short in time, e.g. in the range of 5-10 microseconds. This means that, though the allowed time intervals for measurement is a fairly small part of the total period of 10 milliseconds, several measurements can be performed during these allowed intervals.

In FIGS. 4 to 7 a device is illustrated for measuring eye movements, principally as described in the published International Application WO 86/03113. Here the light detecting element 3 and an IR light emitting element 9, called an eye main IR illuminator, are arranged on a common frame or support 1'. To maintain this support 1' at a distance from the eye and to close off most of the ambient light, a shield 11 is provided. The light detecting elements 3 and the light emitting elements 9 are arranged in pairs, as is shown in FIGS. 5 and 6. In FIG. 5 is shown the arrangement for measuring the eye movement principally in the horizontal direction, i.e. along the x-axis. In a similar way FIG. 6 shows the location of the light emitting elements 9 and the light detecting elements 3 for measurement of the movement of the eye in a vertical direction or a y-direction. These two arrangements could also be combined, as is shown in FIG. 7, for measuring both in the horizontal and vertical directions, i.e. in the x- and y-directions. It can generally be said that the difference of the signals delivered by two light detectors of a pair is an indication of the position of the eye.

According to the invention, for every light sensor 3, a light injection element 5 is provided, arranged to emit extra light into the associated light detector 3 to make this operate within the linear part of its characteristic.

The different types of illumination are shown in FIG. 4. Here $\phi_D$ is the direct ambient light and $\phi_A$ is the ambient light incident upon the light detecting element 3, also called diffused ambient light. The light emitted from the main light emitting element 9 is $\phi_M$ and it is reflected by the eye to give the reflected light $\phi_R$. The light injected by the light injector 5 into the light sensor 3 is as above $\phi_I$.

In FIG. 9 another arrangement is illustrated, intended for measuring the eye movements in the vertical or y-direction. The device is shown from the side of the device facing the eye, whose movements are to be determined. On a frame 1'', provided with a centrally located aperture 2, in this case of a generally rectangular shape, there are arranged two light detecting elements 3, two light injecting elements 5 located adjacent to each light detector and two light emitting elements 9. The light detecting elements 3 are arranged symmetrically with respect to the eye in a vertical plane or y-plane passing through the symmetry point of the eye. Next, the light emitting elements 9 are arranged on a horizontal axis or x-axis of the same kind. These light emitting elements 9 are also arranged symmetrically with respect to the eye.

In FIG. 10 a similar set of cooperating light emitting elements 9' and light detecting elements 3' and light injectors 5' for measuring the movements of the eye in a horizontal direction is illustrated. In this case the light detecting elements 3' together with the light injecting devices 5' are located in a horizontal plane and the light emitting elements 9' are located in a vertical plane.

In FIG. 8 is shown how the sets of light emitting elements and light detecting elements of FIGS. 9 and 10 could be combined into a device intended for measurement of the eye movements both in a horizontal and a vertical direction, that is along both the x- and y-axis. This device is obtained by superimposing the sets of light emitting and detecting elements of FIGS. 9 and 10 upon each other and on the common frame 1''. When a connected supervising electronic unit stimulates the eye to move in a vertical direction, that is the y-direction, only the set of light emitting elements according to FIG. 9 is activated. When the eye is stimulated to move in a horizontal direction, i.e. the x-direction, the set of light-emitting elements corresponding the set depicted in FIG. 10 is activated. When the eye moves in directions which are not near either of these directions both sets will be activated alternatively, but in these cases e.g. a pulse delivered by the light emitting elements 9 will be issued first and detected by the light detecting elements 3 and after that a pulse will be emitted from the light emitting elements 9' and detected by the light detecting elements 3'. In this case a good separation of the eye movement into the two components of the movement along the horizontal and vertical axes will be achieved.

It is obvious that the highly advantageous arrangement according to FIGS. 8–10 also can be used in the same way as the device according to the cited Internation Application WO 86/03113, i.e. without the use of injecting extra light by the injecting elements 5 and 5'.

In FIG. 11 is schematically illustrated how a system for measuring the movements of an eye or eyes could be configured. The support 1' with its attached main eye illuminating element 9, the light detecting element 3 and the element for injecting light 5 are controlled by a microprocessor 13 provided with all necessary driving, interfacing, converting and analyzing circuits. There is also provided a visual stimulus consisting of a display screen 15, which is e.g. an ordinary screen of the type used in television sets. On this screen 15 pictures are produced, for instance a small spot, which could be blinking, to be looked upon when calibrating the equipment. Attached to the television screen 15 are also an ultrasonic ranging device 17 adapted to measure the distance from the eye to be measured to the television screen, and an IR headlight 19, which produces an IR light beam intended to be used when measuring the movements of the head of the person to be tested. This headlight 19 acts as an artificially enhanced ambient light source.

The system according to FIG. 11 operates in the following way, compare FIG. 12, where is illustrated the light detector response signal as a function of time for measurements in the x-direction. The period (10 milliseconds) of the ambient light fluctuations is divided into two equal halfs, the first A for measuring the eye movement in the x-direction and the second half B for measuring in the vertical direction. During each half period three measurements are performed. These are activated by energizing or changing the amount of light, delivered by one of the light emitting elements provided in the system. The pulse period will in this case be about one third of the half period, i.e. with a 50 Hz mains supply and a half period of 5 milliseconds, a pulse length d of about 1.5 milliseconds. At the end of each pulse $p_1$, $p_2$, $p_3$ the corresponding measurement is undertaken by sampling the signal of the light detector during a sufficiently small time, and as mentioned this can be about 5 to 10 microseconds. A pulse length of a sufficient length is required in order to allow the associated light and electric transient components to decay. The first pulse $p_1$ during each half period could for instance be delivered by the light emitting elements 9, the main illuminators, and during the first period these light emitters correspond to the light detecting elements for the horizontal direction, shown in FIGS. 5 and 10. At the end $e_1$ of this pulse $p_1$ the signal indicative of the eye movement along the x-axis is obtained from the light detecting element 3. Next, the amounts of light delivered by the injecting elements 5 are changed ($p_2$) a little in order to allow a test to be performed, whether the associated light detectors 3 are working on the linear part of the characteristic. The detector signal is obtained at the end $e_2$ of this time period $p_2$ having the injected light amount changed. The last pulse $p_3$ of the first half period is delivered by the IR head light 19. At the end $e_3$ of this pulse $p_3$ the signals delivered by the light sensors also contain an indication of the position of the head.

In the case just described, the measurements are performed within a time period of a length slightly more than three milliseconds, and these measurements could be triggered, by means of the above mentioned extra light detector or a detector connected to the mains supply, to fall within that period when the ambient light is within the linear portion of the characteristic of the detector elements 3. This means that in some cases it may be necessary to offset the measuring half periods A and B in regard of the corresponding half periods of the ambient light fluctuations.

In the case where the ambient light is substantially of DC-type and has no rapid variations, the measuring rate could be much higher, up to about 500 measurements per second.

In general, the eye position signal for the position of the eye in the x- or horizontal direction, i.e. principally the difference between the output signals of the light detecting elements 3 or 3' intended for this measurement, compare FIG. 4, primarily depends on the following factors:

1. The distance of the IR main light emitting element 9 or 9' to the eye.
2. The contrast between the iris and the sclera.
3. The position of the eye in the horizontal direction.
4. The position of the eye in the vertical or y-direction, also called the cross-talk from the vertical position.
5. The amplitude of the main eye illumination, i.e. of the light provided by the light emitting elements 9, 9'.

The eye position signal in the horizontal direction is also, but in a substantially smaller amount, depending on the following factors:

6. Fine changes of the eye or reflectivity of the eye cavity caused by the flow of blood.
7. The displacement of the light emitting and detecting elements due to the play of the facial muscles.
8. Changes of the ambient light due to e.g. light fluctuations caused by the AC mains supply.
9. The changes of the position of the IR light detecting elements in relation to the ambient light source, which are caused by the movements of the head of the person, whose eye movements are to be measured.

The signal of the position of the eye in the vertical direction will similarly depend on the corresponding entities associated with this direction.

Since the signals of the measurement have a relatively complicated functional dependence on many factors a calibration procedure can be undertaken for each axis. However, in many cases it will be satisfactory to use the difference signal for a pair of light detectors 5 or 5' as a measure of the eye position. Generally, it has been found that with the equipment according to the invention this will give measured values having an estimated error less than ±5%. For the calibration a system according to FIG. 11 is used. On the display 15 some figure to be observed as for instance a light spot is projected. The person, whose eye movements are to be measured, is then instructed to look at this object as smoothly as possible. The calibration steps are listed in the table below.

| Cross calibration procedure for the x-axis | |
|---|---|
| HEAD & EYE MOVEMENT TASK CONDITIONS | CALIBRATION TASK |
| Head steady Eye or eyes fixate a fixed blinking spot | Adjusting injection offset Testing linearity Ambient light compensation - injection level |
| Head steady Eye or eyes follow a saccadic target displaced along the horizontal axis (x) | Evaluating saccadic responses Adjusting main eye illumination Retesting linearity Main IR off - IR headlight on Evaluating saccadic responses Preparing table of corrections |
| Head steady Eye or eyes follow a saccadic target displaced along the vertical axis (y) | Main IR on - IR headlight off Evaluating x responses Preparing cross-talk table Retesting linearity |
| Rotating head horizontally while fixation of the eye or eyes on a blinking fixed spot | Main IR on alternatively with IR headlight Recording the eye movement signal Recording the ambient light changes caused by the head rotation |
| Avoking the VOR (Vestibulo Ocular Reflex) | Using the eye movement signal to calibrate ambient light changes as a measure of the head rotation |
| The eye or eyes move the same angular amount as the head but in opposite directions | Continuous recording of absolute calibaration responses to check against abrupt non-linearities |

Some comments on this table are given below.

In the first step it is tested if the light detecting elements are working on the linear part of their characteristic. For this purpose the amount of light injected by the injecting elements 5, 5' are changed in steps and the corresponding output signal from the light detectors 3 are analyzed. For such an analysis there has to be performed measurements for at least two different steps of change of the injecting elements 5. The differences of this measured values and the unchanged value are compared. If e.g. the steps have such values that one is half the other one, also the measured differences should have this relationship. The detection offset mentioned in the first step is defined as the difference of the amount of light injected by the two injecting elements 5 or 5' for a specific direction, in this case the x-direction, and the injection level is the average of these amounts. Generally, the light injected by these two elements 5 or 5' can be changed in one of two ways:

With a given average level of injected light each injector 5 can be changed upwards and downwards if the other injector is changed in the opposite direction and in the same amount. Sometimes these balanced changes are not enough, so that the average level or injection level also has to be changed.

In the second step the head is held steady and the person, whose eye movements are to be measured, is instructed to let his eye or eyes follow a target, e.g. a blinking spot, which is displaced stepwize on the screen along the horizontal axis. It may be sufficient to first show the blinking spot at the centre of the screen, next in a position to the left of the centre, then again in the middle and finally in a position to the right of the centre. A complex pattern may be found when a person with his look follows an object which is displaced stepwize and some care has to taken to find out the correct measured value for the spots when these are suddenly displaced to a new position. Since these spots preferably may be located adjacent to the boundary of what could be shown on the screen, the output signals for these positions also are expected to be boundary values of the output response and then the main eye illumination could be adjusted. That is, the main eye illumination would be decreased for instance if it is observed that the light detectors or their associated electronic components are driven to saturation in one of the end positions. In the second part of this second step the main eye illumination is turned off and instead the IR headlight 19 is turned on. For the same stepwize displacement of the blinking target the response of the light detecting elements is observed and in this way a table of corrections could be prepared, showing the influence due to the position of the eye in ambient light. The table of corrections thus gives the corrections of the main characteristic of the eye movements, which are caused by the reflections by the eye of the ambient light.

The calibration operations in the first and second part of the secont step could of course be performed by using the above described interleaving method, alternatingly using one measuring period having only the main eye illumination turned on and another measuring period having only the headlight turned on.

After adjusting the main eye illumination again the linearity of the detector response has to be tested again. This is done in the way described above and according to the results the main eye illumination could be adjusted.

In the third step the person is instructed to keep his head steady and his eye or eyes should follow the blinking spot which is displaced stepwize along the vertical axis. The blinking spot could move in a similar way as for the x-axis, that is from the central location to a place above this adjacent to the border of the screen and next again to the centre of the screen and finally the spot is moved to a position below the centre point adjacent to the screen border. During this the main eye illumination is turned on and the light detector response is evaluated. Normally this detector signal will be small and from this a cross-talk table is established. This cross-talk table gives the influence of the eye position in the vertical direction on the signal for the position in the horizontal direction.

In the fourth step the measurement system is calibrated with regard to the movement of the head. For this the main eye illumination is turned on alternatively with the IR headlight. The person, whose eye movements and possibly also head movements are to be measured, is instructed to rotate his head in a horizontal plane while he fixates with one eye or both the fixed blinking spot. In this way the so called vestibular ocular reflex is used. This will mean that the eye or eyes move in the opposite direction to the head. For a distant object, also the movement of the eye or eyes will have the same amount as the movement of the head. The eye movement signal is recorded and also the ambient light, which are caused by the rotation of the head. From the eye movement signal, the rotation of the eyes can be calculated. If the distance of the screen to the eyes is known and the distance of the eyes to the swinging axis of the head is known, the movements can be calculated easily by trigonometry. However, as is already mentioned, roughly the rotations of the eyes and the head can be taken as equal in degrees. In this simple way a measured value of the head movement is obtained, just by fastening a pair of special goggle-like frames to the person's head and having him look at the screen pictures.

As a last part of this calibration task the response of the light detectors is observed continuously and these signals are checked and recorded. Is is generally observed that the recordings obtained are smooth and behave as expected without any steps or non-linearities.

In FIG. 13 is illustrated a block diagram of the circuitry associated with the measurements. Only the circuits needed for measuring in the x-direction for one eye are illustrated and it should be understood that for the other measurements, that is for the same eye in the x-direction and for the other eye in the x- and y-directions, similar circuitry is used and this is indicated by the three dashed lines connected to the common bus line.

The main IR illuminators 9' are connected in series and their voltage is regulated by a light servo driver 21. This servo driver 21 provides a stabilized voltage to the eye illuminators 9' by using similar light diodes as 9' which are placed inside a closure and these secondary compensating light emitting diodes emit radiation which is sensed by infrared detectors placed inside the same closure. The current flowing through these light detector is sensed and used to regulate the light delivered by the light emitting elements 9'.

The main eye illuminators 9' obtain their signal, that is information on the driving power, from a digital-to-analog converter 23 which has its input connected to the mentioned bus line 25, which as shown could be a common IBM bus inside an IBM compatible personal computer 27. The D/A-converter 23 is also controlled by a counter/timer 29 which provides the neccessary timing signals for all components of the system outside the computer 27.

The light injecting diodes 5' are in the same way connected to digital-to-analog converters 31 which also are connected to the IBM bus 25 and are controlled by the timer 29. Of course there also has to be some driver circuits (not shown) provided for these light emitting diodes 5'.

Finally the light detectors 3' are connected in series to a balanced voltage +V and −V and from their common junction there is a line to a differential amplifier 33. This differential amplifier has its output connected to an analog-to-digital converter 35 and this in turn is connected to the IBM bus 25. The differential amplifier 33 consists of two operational amplifiers (not shown), one used for voltage stabilization in a network comprising two Zener diodes connected in parallel to the light detecting diodes 3' and a second operational amplifier used for amplifying the difference signal.

As is indicated in FIG. 13 with dashed lines, on the support 1", all the light emitting and detecting elements are placed and also said differential amplifier with its operational amplifiers and its other network components such as diodes, resistors and capacitors.

Also shown in FIG. 13 are the ultrasonic distance measuring device 17 which is controlled by the counter/timer 29. The headlight 19 has its own driver circuit connected to the computer 27 and controlled by the timer 29.

It should be emphasized that several driver circuits, addressing and swithing circuits are not shown in FIG. 13. For instance some of the D/A- or A/D-converters used for the measurement in one direction for one eye could be used for measurements in other directions or for the other eye if a suitable switching network is supplied.

We claim:

1. A process for the measurement of light, where the incident light is derived from a first light source and is composed of background light, changing relatively slowly, and rapidly changing light variations, wherein a light sensitive element is used to produce a signal, indicative of the incident light comprising the steps of:
   arranging a separate extra first light emitting element to emit extra light into said light sensitive element; and
   controlling the amount of said extra light emitted from said light emitting element so as to cause the sum of said extra light and said background light, incident upon said light sensitive element, to be substantially constant.

2. A process according to claim 1, wherein the providing of light from said first light source is by providing an artificial light source together with ambient light.

3. A process according to claim 2, wherein the providing of light from said artificial light source is provided by light which is emitted from a second light emitting element and which is reflected from an object to be monitored.

4. A process according to claim 1, further comprising:
   locating a separate extra first light emitting element adjacent to the light sensitive element in such a way that the light from this separate light emitting element directly enters said light sensitive element without being reflected by any objects in the neighborhood.

5. A process according to claim 1, wherein said light variations are equal to zero in predetermined time intervals, and said background light is measured during said predetermined time intervals and that this measurement is used for the control of said first light emitting element.

6. A process according to claim 1, for use in measuring the movements of an eye of a person,
   wherein the incident light comprises light derived from at least one second light emitting element which is placed at some distance from the eye to emit light changing rapidly, and said rapidly changing light variations incident upon the light sensitive element are essentially the light, which is emitted by said at least one second light emitting element and then is reflected by the eye upon the surface area of said light sensitive element, and
   said background light comprises the ambient light.

7. A device for the measurement of variations in incident light, where the incident light is composed of background light, changing relatively slowly, and rapidly changing light variations, comprising a light sensitive element producing a signal, indicative of the incident light,
   wherein a separate first light emitting element is arranged to emit extra light into said light sensitive element, this first light emitting element being located in such a way that the extra light will pass directly to the surface of the light sensitive element and is not disturbed by any objects in the neighborhood, and
   the amount of said extra light emitted from said first light emitting element is controlled to cause the sum of said extra light and said background light, incident upon said light sensitive element, to be substantially constant.

8. A device according to claim 6 wherein said first light emitting element is located adjacent to the light sensitive element.

9. A device according to claim 6, wherein said light sensitive element is substantially planar and said first light emitting element is placed adjacent to one edge of said light sensitive element.

10. The use of the device according to claim 6, in measuring eye movements of a person,
wherein at least one second light emitting element is located to emit varying light on to said person's eye,
said light variations being the light reflected by the person's eye and derived from said second light emitting element and
the background light being the ambient light, and said reflected light and the ambient light and the light upon said light sensitive element derived from said first light emitting element, directly impinging onto said light sensitive element, are measured by means of said light sensitive element.

11. A process for the measurement of variations in incident light, comprising the steps of:
deriving the incident light source and wherein said incident light is comprised of background light, which changes relatively slowly, and rapidly changing light variations,
producing a signal from a light sensitive element indicative of the incident light;
arranging a first light emitting element to emit extra light into said light sensitive element, the amount of said extra light emitted from said light emitting element being controlled to cause the sum of said extra light and said background light, incident upon said light sensitive element, to correspond to an amount of light, which is located on a substantially linear portion of the characteristic curve of the light sensitive element.

12. A process according to claim 11, wherein the providing of light from said first light source is by way of an artificial light source together with ambient light.

13. A process according to claim 12, wherein the providing of light from said artificial light source is by way of light which is emitted from a second light emitting element and which is reflected from an object to be monitored.

14. A process according to claim 11, further comprising: choosing a location on the substantially linear portion in such a way that the sum of said rapidly changing light variations and said sum of said extra light and said background light also corresponds to an amount of light, which is located on said linear portion of the characteristic of the light sensitive element.

15. A process according to claim 11, for use in measuring the movements of an eye of a person further comprising:
placing at least one second light emitting element at some distance from the eye to emit light changing rapidly and said rapidly changing light variations incident upon the light sensitive element are essentially the light, which is emitted by said at least one second light emitting element and then is reflected by the eye upon the surface area of said light sensitive element; and
wherein said background light is the ambient light.

16. A procedure for calibrating the measurement process according to claim 11 further comprising:
changing the amount of said emitted extra light in at least one step of known size,
analyzing the output signal of said light sensitive element is in order to establish if the output signal is proportional to or has a linear dependance of the total amount of light incident upon said light sensitive element, when said background light is kept constant, and
changing the amount of said extra light if said analysis shows, that the light sensitive element is not operating at a linear portion of its characteristic.

17. A procedure according to claim 16, wherein said changes of the extra light are at least two and that the differences between the output signals for these changed amounts of extra light and the output signal before these changes are used in said analysis for linearity.

18. A device for the measurement of variations in incident light, where the incident light is composed of background light, changing relatively slowly, and rapidly changing light variations, comprising a light sensitive element producing a signal, indicative of the incident light,
wherein a first light emitting element is arranged to emit extra light into said light sensitive element, this first light emitting element being located in such a way that the extra light will pass directly to the surface of the light sensitive element and is not disturbed by any objects in the neighborhood, and
the amount of said extra light emitted from said first light emitting element is controlled to cause the sum of said extra light and said background light, incident upon said light sensitive element, to correspond to an amount of light, which is located on a substantially linear portion of the characteristic carve of the light sensitive element.

19. A device according to claim 18, wherein said first light emitting element is located adjacent to the light sensitive element.

20. A device according to claim 19, wherein said light sensitive element is substantially planar and said first light emitting element is placed adjacent to one edge of said light sensitive element.

21. The use of the device recording to claim 18, in measuring eye movements of a person,
wherein at least one second light emitting element is located to emit varying light on to said person's eye,
said light variations being the light reflected by the person's eye and emitted by said second light emitting element and the background light being the ambient light, and said reflected light and the ambient light and the light upon said light sensitive element derived from said first light emitting element, directly impinging onto said light sensitive element, are measured by means of said light sensitive element.

* * * * *